United States Patent
Chino et al.

(10) Patent No.: US 11,379,976 B2
(45) Date of Patent: Jul. 5, 2022

(54) MEDICAL IMAGE PROCESSING APPARATUS, MEDICAL IMAGE PROCESSING METHOD, AND SYSTEM FOR TISSUE VISUALIZATION

(71) Applicant: ZIOSOFT, INC., Tokyo (JP)

(72) Inventors: Shusuke Chino, Tokyo (JP); Tsuyoshi Nagata, Tokyo (JP); Satoshi Shimizu, Tokyo (JP); Yasuhiro Kondo, Tokyo (JP); Yutaka Karasawa, Tokyo (JP); Shinichiro Seo, Tokyo (JP)

(73) Assignee: ZIOSOFT, INC., Tokyo (JP)

( * ) Notice: Subject to any disclaimer, the term of this patent is extended or adjusted under 35 U.S.C. 154(b) by 139 days.

(21) Appl. No.: 16/839,399

(22) Filed: Apr. 3, 2020

(65) Prior Publication Data

US 2020/0320696 A1 Oct. 8, 2020

(30) Foreign Application Priority Data

Apr. 4, 2019 (JP) .............................. JP2019-072301

(51) Int. Cl.
*G06T 7/00* (2017.01)
*G06T 7/62* (2017.01)
(Continued)

(52) U.S. Cl.
CPC ............ *G06T 7/0012* (2013.01); *A61B 6/032* (2013.01); *A61B 6/463* (2013.01); *G06T 7/62* (2017.01);
(Continued)

(58) Field of Classification Search
None
See application file for complete search history.

(56) References Cited

U.S. PATENT DOCUMENTS

| 2004/0101104 A1* | 5/2004 | Avinash ................. A61B 6/463 378/98.12 |
| 2006/0103670 A1 | 5/2006 | Matsumoto |

(Continued)

FOREIGN PATENT DOCUMENTS

JP 4188900 B2 12/2008

OTHER PUBLICATIONS

Choi, Jin Woo, et al. "Comparison of Transaxial Source Images and 3-Plane, Thin-Slab Maximal Intensity Projection Images for the Diagnosis of Coronary Artery Stenosis with Using Ecg-Gated Cardiac CT." Korean Journal of Radiology, vol. 7, No. 1, 2006, p. 20., https://doi.org/10.3348/kjr.2006.7.1.20. (Year: 2006).*

(Continued)

*Primary Examiner* — Samah A Beg
*Assistant Examiner* — Courtney Joan Nelson
(74) *Attorney, Agent, or Firm* — Pearne & Gordon LLP

(57) ABSTRACT

A medical image processing apparatus includes: a display unit; and circuitry configured to: acquire volume data including tissues, and set a first mask region and a second mask region which include a voxel to be rendered among a plurality of voxels included in the volume data; set a first plane which intersects both the first mask region and the second mask region; display a first image in which a first region formed by cutting the first mask region by the first plane and the second mask region are rendered; receive through an operation unit a first operation for setting a second plane which is parallel to the first plane and intersects both the first mask region and the second mask region; and display a second image in which a second region formed by cutting the first mask region by the second plane and the second mask region are rendered.

9 Claims, 17 Drawing Sheets

(51) Int. Cl.
  *G06T 15/08* (2011.01)
  *A61B 6/03* (2006.01)
  *A61B 6/00* (2006.01)
  *G06V 10/40* (2022.01)
(52) U.S. Cl.
  CPC .............. *G06T 15/08* (2013.01); *G06V 10/40* (2022.01); *G06T 2207/10081* (2013.01); *G06T 2207/30056* (2013.01); *G06T 2207/30061* (2013.01); *G06T 2207/30096* (2013.01)

(56) References Cited

U.S. PATENT DOCUMENTS

2009/0003668 A1\* 1/2009 Matsumoto ............... G06T 7/60
  382/128
2016/0037087 A1\* 2/2016 Price ..................... H04N 5/272
  348/586

OTHER PUBLICATIONS

Wang, Chunliang, et al. "An Interactive Software Module for Visualizing Coronary Arteries in CT Angiography." International Journal of Computer Assisted Radiology and Surgery, vol. 3, No. 1-2, 2008, pp. 11-18., https://doi.org/10.1007/s11548-008-0160-6 (Year: 2008).\*

\* cited by examiner

MEDICAL IMAGE PROCESSING APPARATUS, MEDICAL IMAGE PROCESSING METHOD, AND SYSTEM FOR TISSUE VISUALIZATION

CROSS-REFERENCE TO RELATED APPLICATIONS

This application is based on and claims priority under 35 USC 119 from Japanese Patent Application No. 2019-072301 filed on Apr. 4, 2019, the contents of which are incorporated herein by reference.

TECHNICAL FIELD

The present disclosure relates to a medical image processing apparatus, a medical image processing method, and a system.

BACKGROUND ART

In the related art, medical image processing apparatuses that generate images of slab regions from volume data have become known (see US Patent Application Publication No. 2009/0003668). The medical image processing apparatus specifies a range of an area of interest of a blood vessel by designating a start point and an end point on the central axial line of the blood vessel. A front point on the frontmost side and a rear point on the rearmost side on a central axial line between a start point and an end point when seen in an imaging direction are obtained. Subsequently, a plane intersecting the front point and located in a front direction with respect to a plane perpendicular to an imaging direction by a predetermined distance is set to be a designated front plane. A plane intersecting the rear point and located in a depth direction with respect to a plane perpendicular to an imaging direction by a predetermined distance is set to be a designated rear plane. A region between the designated front plane and the designated rear plane is set to be a region of interest including an area of interest without missing.

In a slab, a region which is cut by a desired plane in volume data can be created. The extraction of a region using a mask is also known together with the creation of a region using a slab. In a mask, a region can be extracted so as to include a desired voxel in a desired form in volume data. For example, in a case where a plurality of tissues are extracted from volume data using a plurality of masks and only a region included in a slab is visualized for the extracted tissues, a plurality of mask regions are uniformly deleted by the slab.

In this case, the visibility of a tissue that the user desires to observe may be insufficient. For example, in a case where at least a portion of a tissue (for example, a blood vessel) is included in another tissue (for example, an internal organ), both the tissues are visualized so that they are cut at the same location in a planar manner, and thus it is difficult to observe the included tissue.

The disclosure is contrived in view of the above-described circumstances and provides a medical image processing apparatus, a medical image processing method, and a system which are capable of improving the visibility of a tissue to be observed.

SUMMARY

A medical image processing apparatus of the present disclosure includes: a display unit; and circuitry configured to: acquire volume data including tissues; and set a first mask region and a second mask region which include a voxel to be rendered among a plurality of voxels included in the volume data; set a first plane which intersects both the first mask region and the second mask region; display through the display unit a first image in which a first region formed by cutting the first mask region by the first plane and the second mask region are rendered; receive through an operation unit a first operation for setting a second plane which is parallel to the first plane and intersects both the first mask region and the second mask region; and display a second image in which a second region formed by cutting the first mask region by the second plane and the second mask region are rendered.

According to the disclosure, it is possible to improve the visibility of a tissue to be observed.

DESCRIPTION OF EMBODIMENTS

Hereinafter, an embodiment of the disclosure will be described using drawings.

Figure 1:
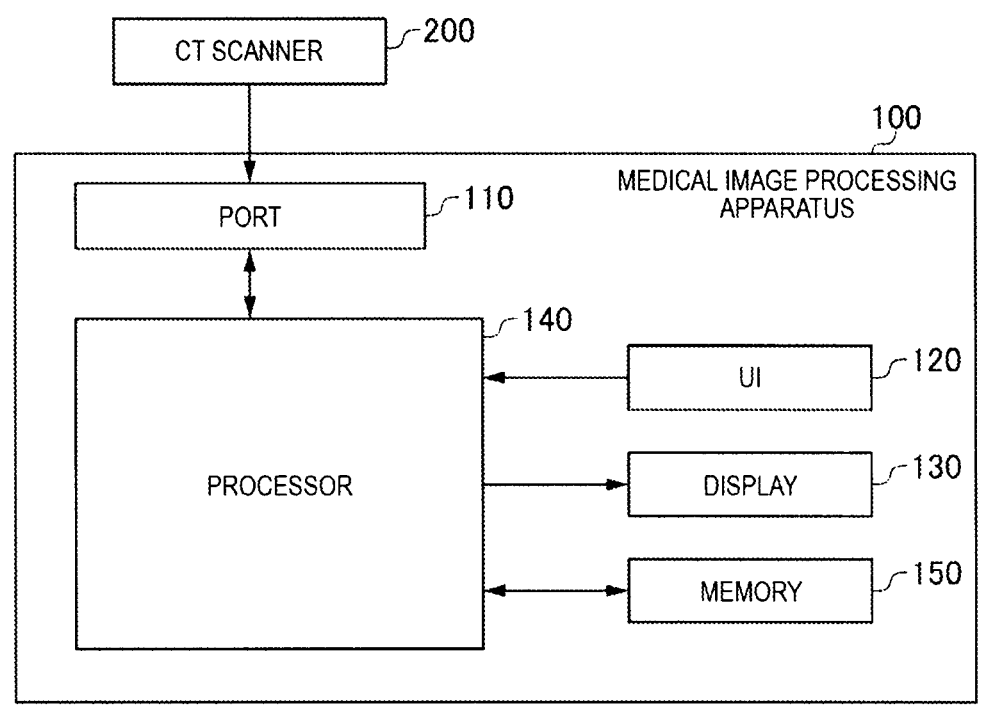
FIG. 1 is a block diagram showing a hardware configuration example of a medical image processing apparatus in an embodiment.

FIG. 1 is a block diagram showing a configuration example of a medical image processing apparatus 100 in an embodiment. The medical image processing apparatus 100 includes a port 110, a UI 120, a display 130, a processor 140, and a memory 150.

A CT scanner 200 is connected to the medical image processing apparatus 100.

The medical image processing apparatus 100 acquires volume data from the CT scanner 200 and performs processing on the acquired volume data. The medical image processing apparatus 100 may be configured by a PC and software loaded into the PC.

The CT scanner 200 irradiates a subject with X rays to capture an image (CT image) using a difference in the absorption of X rays by a tissue in a body. The subject may include a living body, a human body, an animal, and the like. The CT scanner 200 generates volume data including information of any location inside a subject. The CT scanner 200 transmits volume data as a CT image to the medical image processing apparatus 100 through a wired line or a wireless line. In capturing a CT image, imaging conditions related to CT imaging and contrast radiography conditions related to injection of a contrast medium are not taken into consideration.

The port 110 in the medical image processing apparatus 100 includes a communication port, an external apparatus connection port, and a connection port for an embedded device, and acquires volume data obtained by the CT scanner 200. The acquired volume data may be immediately transmitted to the processor 140 to be subjected to various processes, or may be stored in the memory 150 and then transmitted to the processor 140 when necessary to be subjected to various processes. The volume data may be acquired through a recording medium or recording media. The volume data may be acquired in the form of intermediate data, compressed data, or synogram data. The volume data may be acquired from information obtained from a sensor device attached to the medical image processing apparatus 100. The port 110 functions as an acquisition unit that acquires various data such as volume data.

The UI 120 may include a touch panel, a pointing device, a keyboard, or a microphone. The UI 120 receives any input operation from a user of the medical image processing apparatus 100. The user may include a doctor, a radiologist, a student, and other paramedic staffs.

The UI 120 receives various operations. For example, the UI receives operations such as the designation of a region of interest (ROI) and the setting of luminance conditions in volume data or an image (for example, a three-dimensional image or a two-dimensional image to be described later) based on the volume data. The region of interest may include regions of various tissues (for example, a blood vessel, a bronchus, an internal organ, an organ, a bone, and a brain). The tissues may include a disease tissue, a normal tissue, a tumor tissue, and the like. The UI 120 may receive the designation of a point of interest or a portion of interest that a user desires to observe. The UI 120 may receive an operation of changing a view direction for a rendering image or the direction and the position of a slab surface.

The display 130 may include, for example, an LCD and displays various information. The various pieces of information may include a three-dimensional image or a two-dimensional image obtained from volume data. The three-dimensional image may include a volume rendering image, a surface-rendered image, a virtual endoscopic image, a virtual ultrasound image, a CPR image, and the like. The volume rendering image may include a raysum image, an MIP image, a MinIP image, an average value image, or a raycast image. The two-dimensional image may include an axial image, a sagittal image, a coronal image, an MPR image, and the like.

The memory 150 includes various primary storage apparatuses such as a ROM and a RAM. The memory 150 may include secondary storage apparatuses such as an HDD and an SSD. The memory 150 may include cubic storage apparatuses such as a USB memory and an SD card. The memory 150 stores various pieces of information and programs. The various pieces of information may include volume data acquired by the port 110, an image generated by the processor 140, setting information which is set by the processor 140, and various programs. The memory 150 is an example of a non-transitory recording medium in which programs are stored.

The processor 140 may include a CPU, a DSP, or a GPU. The processor 140 functions as a processing unit 160 that performs various processes and controls by executing a medical image processing program stored in the memory 150.

Figure 2:
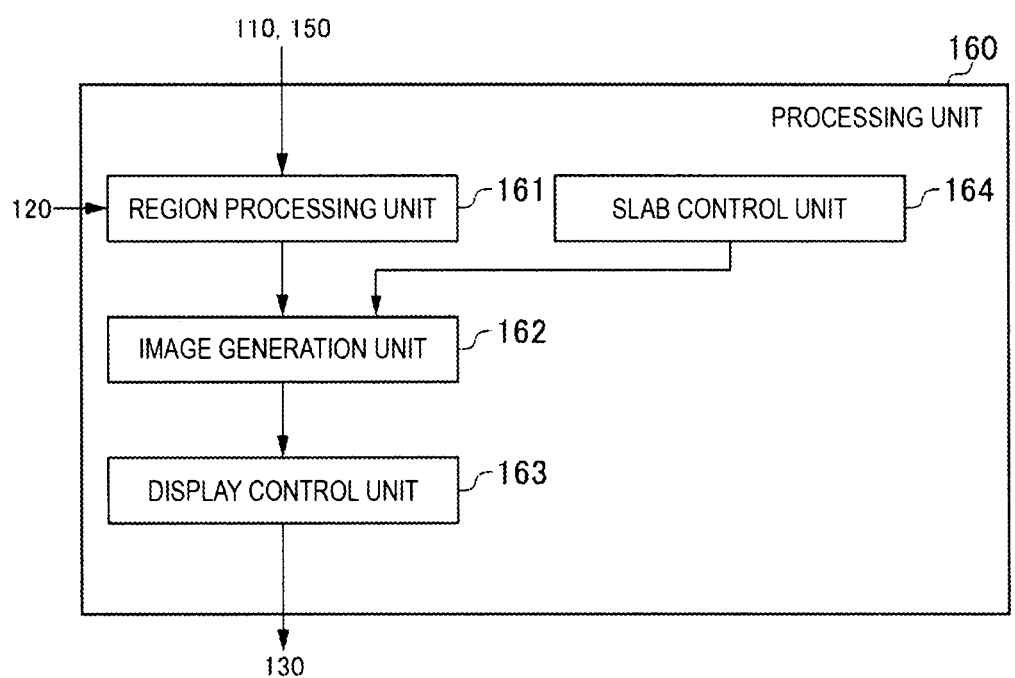
FIG. 2 is a block diagram showing a functional configuration example of the medical image processing apparatus.

FIG. 2 is a block diagram showing a functional configuration example of the processing unit 160.

The processing unit 160 includes a region processing unit 161, an image generation unit 162, a slab control unit 164, and a display control unit 163. Units included in the processing unit 160 may be implemented as different functions by one piece of hardware or may be implemented as different functions by a plurality of pieces of hardware. The units included in the processing unit 160 may be implemented by a dedicated hardware part.

The region processing unit 161 acquires volume data of a subject through, for example, the port 110. The region processing unit 161 extracts any region included in volume data as a mask region. The region processing unit 161 may automatically designate a region of interest on the basis of, for example, a voxel value of volume data and extract a mask region as a region of interest. The region processing unit 161 may manually designate a region of interest through, for example, the UI 120 to extract a region of interest. The region of interest may include regions such as a lung, a liver, a bronchus, a lung artery, a lung vein, a liver artery, a portal vein, and a liver vein. The region of interest may be at least a portion of an internal organ resected from a subject or may be a disease or a tumor.

The slab control unit 164 may set a slab region or a slab surface by a user's operation through the UI 120. In slab control, a slab region is set by being cut along a volume data slab surface. The region processing unit 161 may set a slab surface in a volume space. The slab surface is equivalent to a cutting surface for cutting volume data. One plane may be set as the slab surface. One side in a predetermined region which is cut by the slab surface may be set to be a rendering target, and the other plane in the predetermined region may be set to be an out-of-target for rendering. Two parallel planes may be set as the slab surface. A region interposed between two slab surfaces in the predetermined region may be set to be a rendering target, and a region which is not interposed between two slab surfaces in the predetermined region may be set to be an out-of-target for rendering.

The region processing unit 161 may create a mask region by a user's direct operation through the UI 120. The mask region may be visualized by a set of bits corresponding to voxels of volume data on a one-to-one basis. The region processing unit 161 may set a mask region. The mask region is set such that the contour thereof has any shape in three dimensions. A plurality of mask regions may exist. The inside of a mask region is set to be a rendering target, and the outside of the mask region is set to be an out-of-target for rendering. Each mask region may be colored in a different color, or an opacity value corresponding to a voxel value may be set. Image formation using a masking process is disclosed in, for example, Patent Document 1.

(Patent Document 1: Japanese Patent No. 4188900)

Since each three-dimensional position can be designated in detail in a masking process as compared with a slab process, a rendering target can be configured to have a complex shape. Since a slab process can be implemented by storing only positional information of a surface in a three-dimensional space as compared with a masking process, an operation is facilitated, and the amount of calculation can be reduced.

The slab control unit 164 can move a slab surface. For example, a slab surface may be moved in parallel in a direction perpendicular to the slab surface. The slab control unit 164 may receive a user's operation through the UI 120 and move the slab surface.

The slab control unit 164 can rotate a slab surface along a surface parallel to the slab surface. For example, a slab surface may be rotated around a rotation center for rotating the slab surface in volume data. The rotation center may be a central point of a predetermined region in the volume data, a reference point other than the central point, a point of interest, or the like. Even when the rotation center is located on the slab surface, the rotation center may be offset from the slab surface.

The image generation unit 162 may visualize a mask region and a slab region in combination. In this case, a plurality of mask regions may exist, and a slab process may be performed or may not be performed in each of the mask regions. A mask region in which a slab process is performed and a mask region in which a slab process is not performed may be mixed. The image generation unit 162 may designate execution/non-execution of a slab process in each mask region.

The image generation unit 162 generates various images. The image generation unit 162 generates a three-dimensional image or a two-dimensional image on the basis of at least a portion of the acquired volume data (for example, a region extracted from the volume data, or a region in the volume data on which a slab process or a masking process is performed). The image generation unit 162 may generate an image by performing rendering (for example, raycasting or surface rendering) accompanied by ray attenuation. Regarding the three-dimensional image, a superimposition region between a mask region and a slab region may be set as a drawing target.

The display control unit 163 displays various data, information, and images on the display 130. The images include an image generated by the image generation unit 162. The contour or range of a mask region or a slab region may be visualized in a two-dimensional image.

The display of an image which is to be subjected to a slab process and rendered using one slab surface will be also referred to as plain cut. The display of an image which is to be subjected to a slab process using two slab surfaces and rendered between the two slab surfaces may be particularly referred to as slab display. The slab display may include plain cut.

In a slab process, a user only needs to set a slab surface through the UI 120 and does not need to set a mask region, and thus the range of rendering can be limited without setting a mask region in detail. Since the slab process is a dedicated function limited to a plane, both an operation and drawing related to a slab process can be performed at a high speed. A similar function can also be implemented with a combination of masking processes instead of a slab process, that is, a region surrounded by one or more planes can be extracted, but the processing becomes complicated as compared with a slab process. The sum region of a plurality of mask regions is drawn, and a product space of a mask region and a slab region is drawn, thereby making it easier for the user to understand it.

Next, supplementary description for a slab process and a masking process will be given.

In a slab process, a region interposed between two plane (slab surfaces), or only one region separated by the planes is to be rendered and drawn. An operation for a plane is easier than an operation for a space. In a slab process, processing using a surface is performed, so that the burden of processing is small and rendering is performed at a high speed as compared with processing for voxels in three dimensions to which a surface is not applied. This is because, for example, ray imaging can be started from a slab surface. Since redrawing is also performed at a high speed when a slab surface is moved or rotated, it is easy to minutely move or rotate the slab surface. In a case where a slab surface is particularly moved by fixing a parallel view direction to virtual rays for drawing, it is possible to perform drawing by using the previous rendering results again.

In a masking process, drawing is performed with information regarding whether to perform drawing allocated for each voxel of volume data. For this reason, a complicated shape can be visualized, but time and effort are required for an operation. A plurality of masking processes may be performed on different mask regions in volume data. Since drawing is performed for each voxel, rendering is performed at a low speed. This is because it is difficult to redraw only a portion when a mask region is changed. This is also because a calculation time is required due to the necessity of applying, for example, a Marching Cube method again to calculate a surface again in the case of surface rendering.

A slab region may be created through a masking process by using a UI for operating a plane as the UI 120. In this case, a slab can be used even in a case where a rendering engine exclusive for a slab process is not provided. A slab process and a masking process can be executed at the same time and can be used separately. An image obtained through a slab process in a raycast method and an image obtained through a masking process performed on the same object may be images that have delicately different results.

Next, supplementary description for a portion of interest and a point of interest will be given.

A portion of interest may be a portion in which a user is interested in observing a patient, that is, a region to be obtained. The portion of interest may be a disease portion such as a tumor, a ligature isolation portion, or the like. The portion of interest may be a point to be observed, and in this case, the portion of interest and the point of interest are the same. The portion of interest may be designated by a user through the UI 120. The portion of interest may be a region of interest. In a case where a portion of interest is a region, a point of interest may be the center of gravity of the region. In a case where a portion of interest is a region, a point of interest may be positioned outside the region. For example, when the region of the left coronary artery is imparted, it is conceivable that a point of interest is positioned at a left ventricular cavity, the central point of an aortic valve, and a cardiac apex.

A point of interest may be the center of rotation in a case where a slab surface is rotated. When a portion of interest is a region, a point of interest is usually positioned on the inner side of the region. A point of interest may be designated by a user through the UI 120. The region processing unit 161 may set a designated point of interest as a seed point and set a region obtained through region extraction as a portion of interest. In this case, even when the region processing unit 161 fails in region extraction of a portion of interest, a point of interest remains and is usable, and thus user convenience is improved. A point of interest may be positioned on the outer side of a portion of interest. For example, in a case where a voxel having a voxel value equal to or less than a threshold value of volume data is excluded from a region which is a portion of interest after the portion of interest is obtained by performing region extraction including a point of interest, the point of interest may not be included in the region which is the portion of interest. A point which is finally operated through the UI 120, a central point of a disease portion which is automatically extracted, or the like may be set as a point of interest.

Figure 3:
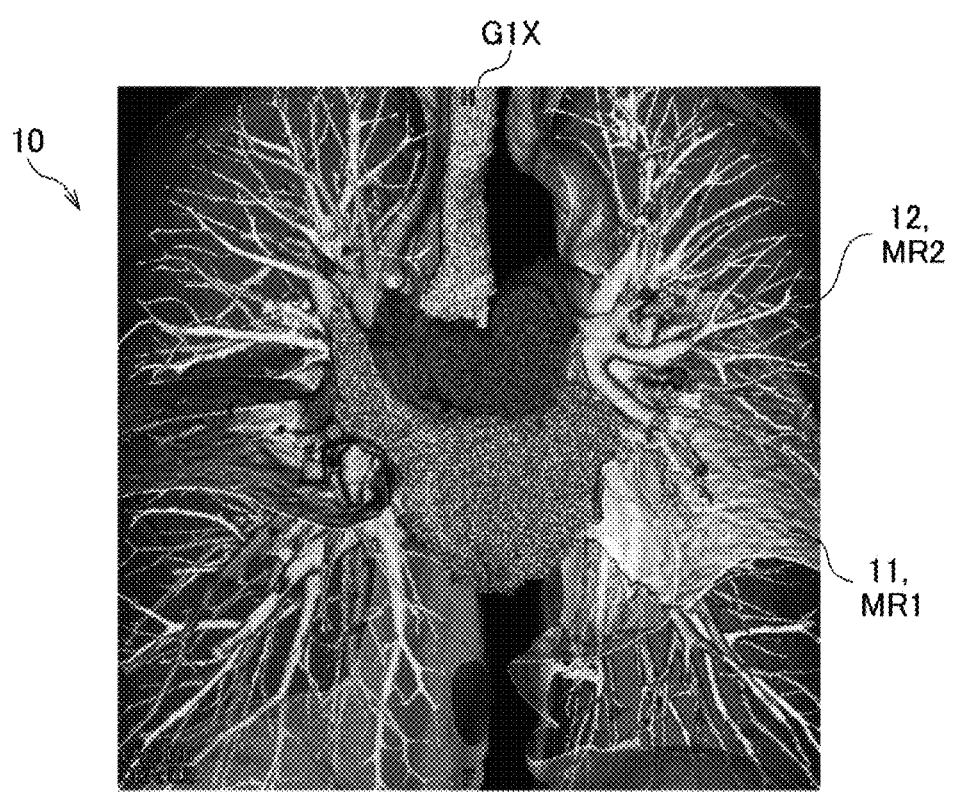
FIG. 3 is a diagram showing a rendering image of a region of a lung in a comparative example.
Figure 4:
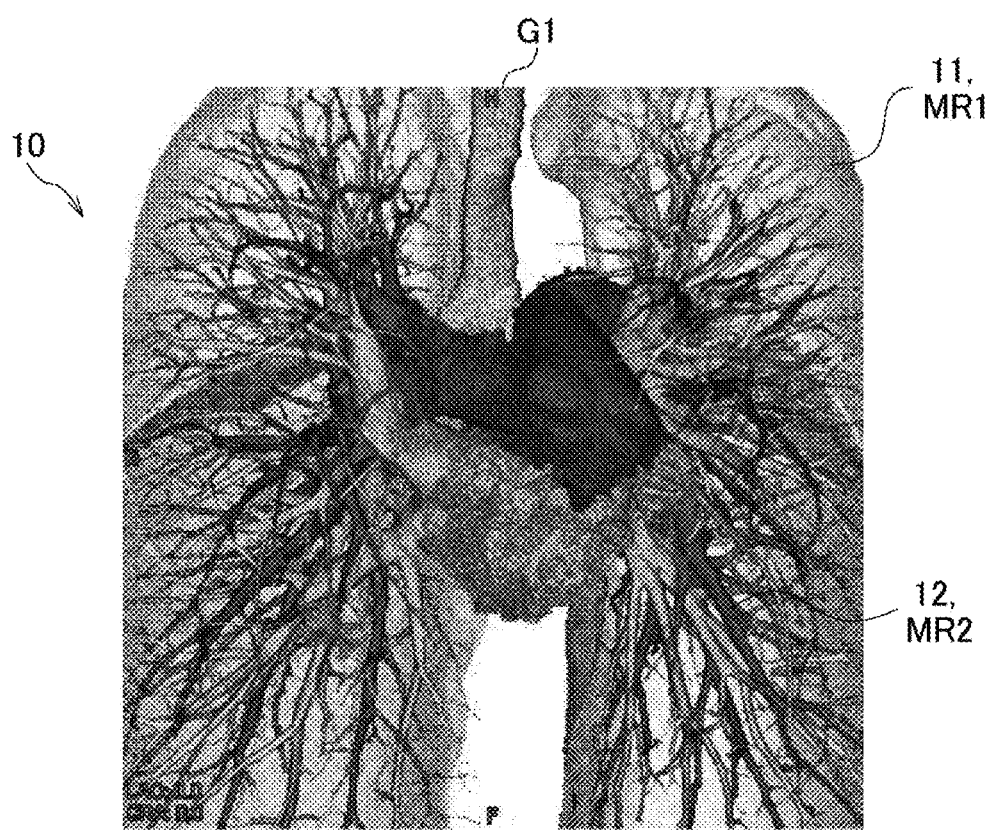
FIG. 4 is a diagram showing an example of a rendering image of a region of a lung in the embodiment.

FIG. 3 is a diagram showing a rendering image G1X of a region 10 of a lung in a comparative example. FIG. 4 is a diagram showing an example of a rendering image G1 of a region 10 of a lung in the present embodiment. In FIGS. 3 and 4, the region 10 of the lung includes lobes of the lung 11 (an example of an internal organ) and blood vessels and the like 12 (an example of a tubular tissue). The blood vessels and the like 12 run inside and outside the lobes of the lung 11. The blood vessels and the like 12 may include a blood vessel (for example, a lung artery and a lung vein), a bronchus, and other tubular tissues. In FIGS. 3 and 4, a mask region MR1 indicating the region of the lobe of the lung 11 is extracted, and a mask region MR2 indicating the region of the blood vessels and the like 12 is extracted. In rendering images G1 and GX1, the lobes of the lung are surface-rendered, and blood vessels and the like are volume-rendered by a raycast method.

In the comparative example, a mask region in which a slab process is performed and a mask region in which a slab process is not performed are not mixed. Thus, both the regions are mask regions in which a slab process is performed or mask regions in which a slab process is not performed. In FIG. 3, the drawing of the lobes of the lung 11 is limited to being performed within the range of a slab, and the drawing of the blood vessels and the like 12 is also limited to being performed within the range of a slab. For this reason, drawing is performed such that the blood vessels and the like 12 are deleted together with the lobes of the lung 11 on the front side of a slab surface (not shown). Accordingly, in FIG. 3, both the lobes of the lung 11 and the blood vessels and the like 12 on the front side of the slab surface are deleted, and it can be understood that less blood vessels and the like are drawn as compared with FIG. 4.

On the other hand, in the present embodiment, a mask region in which a slab process is performed and a mask region in which a slab process is not performed are mixed. In FIG. 4, the drawing of the lobe of the lung 11 are limited to being performed within the range of a slab, and the drawing of the blood vessels and the like 12 does not relate to the inside and outside of the range of a slab. For this reason, a front side of a slab surface (not shown) in the mask region MR1 is set to be an out-of-target for rendering, and the front side of the lobes of the lung 11 is deleted. On the other hand, a slab process is not performed in the mask region MR2, both the front side and the rear side of the slab surface are set to be rendering targets, and the front side of the blood vessels and the like 12 is not deleted. Accordingly, in FIG. 4, the lobes of the lung 11 on the front side of the slab surface are deleted, but blood vessels are not deleted. Thus, it can be understood that more blood vessels are drawn as compared with FIG. 3.

Figure 5:
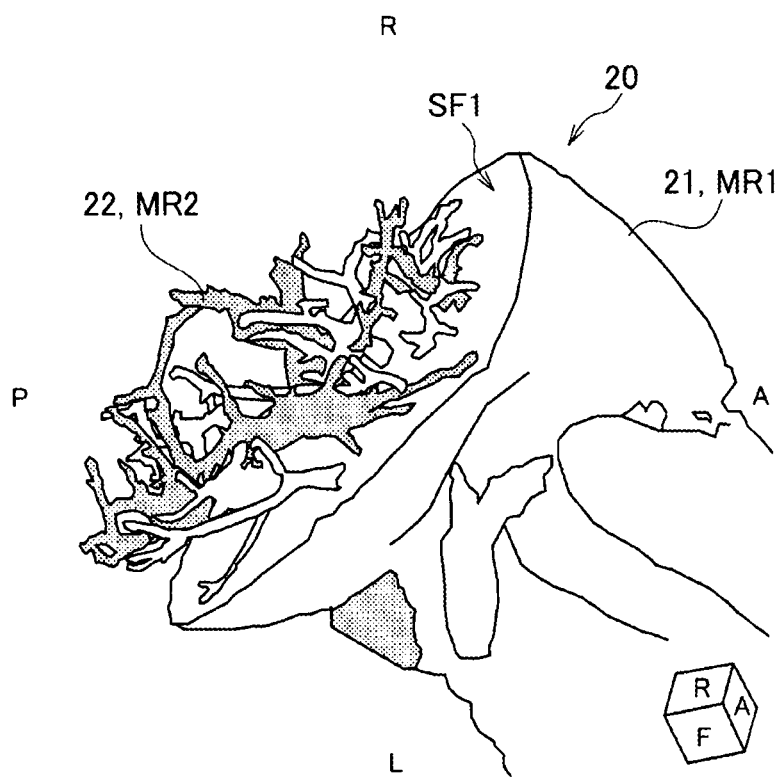
FIG. 5 is a side view showing an example of a rendering image of a region of a liver when seen from the side of a slab surface.
Figure 6:
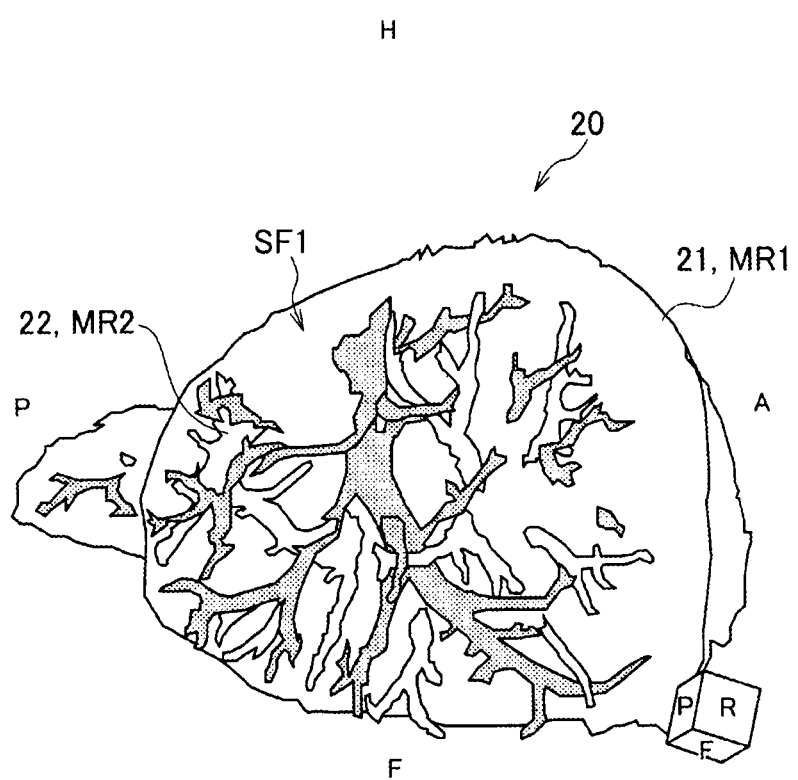
FIG. 6 is a front view showing an example of a rendering image of a region of a liver when seen from the front of a slab surface.

FIGS. 5 and 6 are diagrams showing an example of a rendering image of a region 20 of a liver. FIG. 5 is a diagram when a slab surface SF1 is seen from the side. FIG. 6 is a diagram when the slab surface SF1 is seen from the front. In FIGS. 5 and 6, the region 20 of the liver includes a liver parenchyma 21 (an example of an internal organ) and the blood vessels and the like 22 (an example of a tubular tissue). The blood vessels and the like 22 run inside and outside the liver parenchyma 21. The blood vessels and the like 22 may include a liver artery, a portal vein, a liver vein, and other tubular tissues. In a rendering image G2, raycasting is performed on both the liver parenchyma 21 and the blood vessels and the like 22.

In FIGS. 5 and 6, the drawing of the mask region MR1 obtained by extracting the region of the liver parenchyma 21 is limited to being performed within the range of a slab, and the mask region MR2 obtained by extracting the region of the blood vessels and the like 22 is drawn regardless of the inside and outside of the range of the slab. For this reason, a front side of a slab surface in the mask region MR1 is set to be an out-of-target for rendering, and the front side of the liver parenchyma 21 is deleted. On the other hand, a slab process is not performed in the mask region MR2, both the front side and the rear side of the slab surface are set to be rendering targets, and the front side of the blood vessels and the like 12 is not deleted. Accordingly, in FIGS. 5 and 6, it is easy to view the blood vessels and the like 22 on the front side of the region 20 of the liver. When the slab surface is moved in a view direction as will be described later, it becomes easier to view the state of the blood vessels and the like 22.

Next, an example of movement of a slab surface will be described.

Figure 7A:
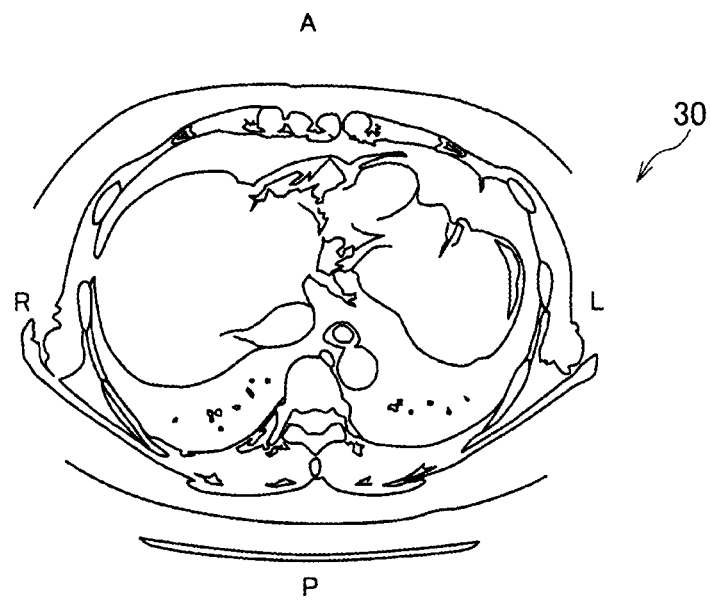
FIG. 7A is a diagram showing an example of an MPR image of a region of a liver (no slab surface)
Figure 7B:
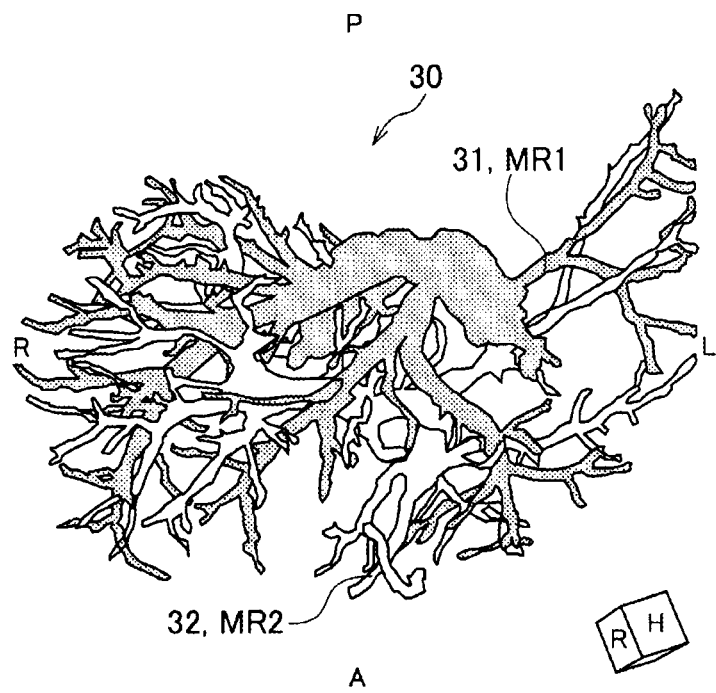
FIG. 7B is a diagram showing an example of a rendering image of a region of a liver corresponding to FIG. 7A.
Figure 8A:
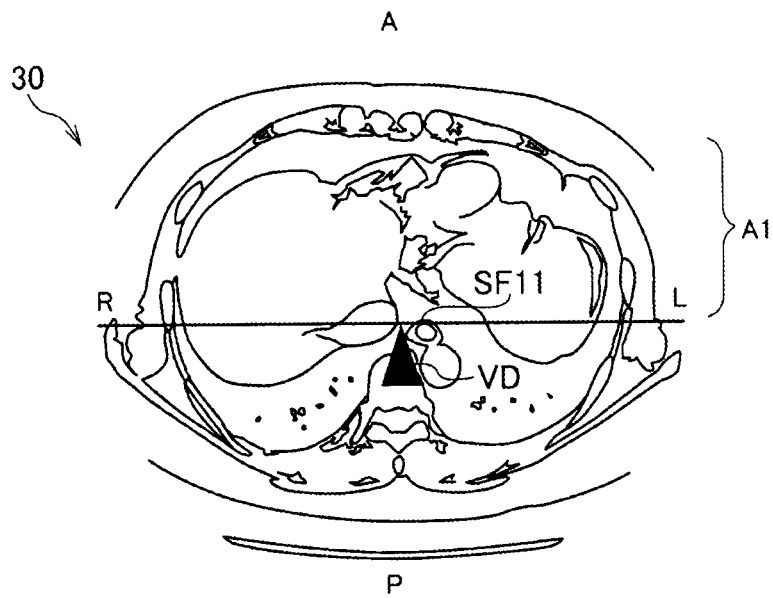
FIG. 8A is a diagram showing a first example of an MPR image of a region of a liver according to the movement of a slab surface.
Figure 8B:
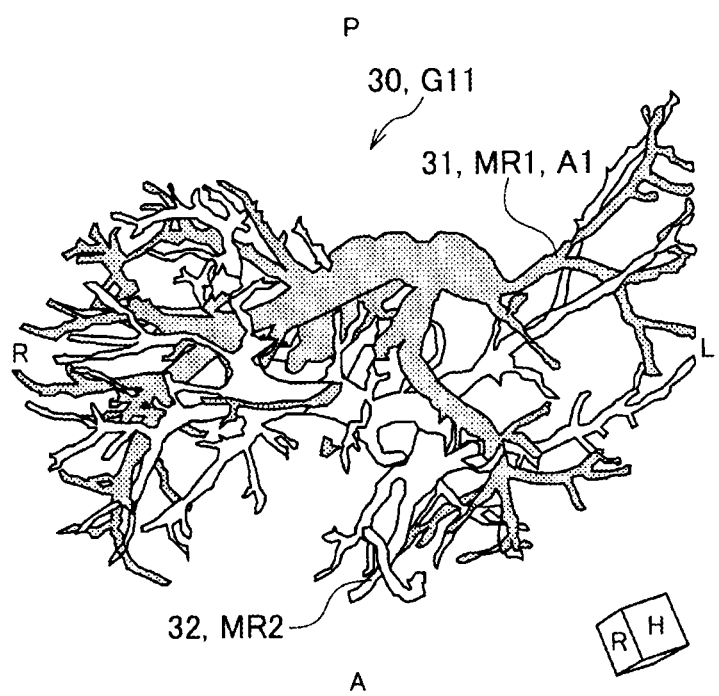
FIG. 8B is a diagram showing an example of a rendering image of a region of a liver corresponding to FIG. 8A.
Figure 9A:
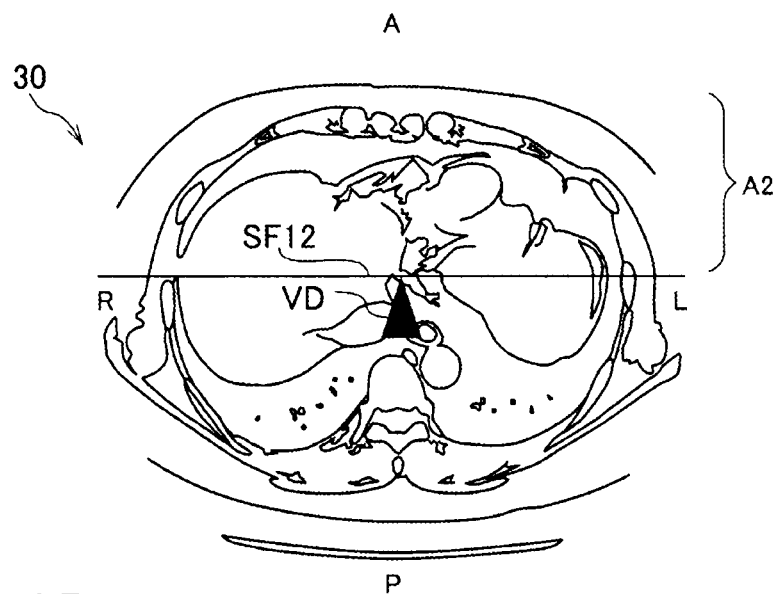
FIG. 9A is a diagram showing a second example of an MPR image of a region of a liver according to the movement of a slab surface.
Figure 9B:
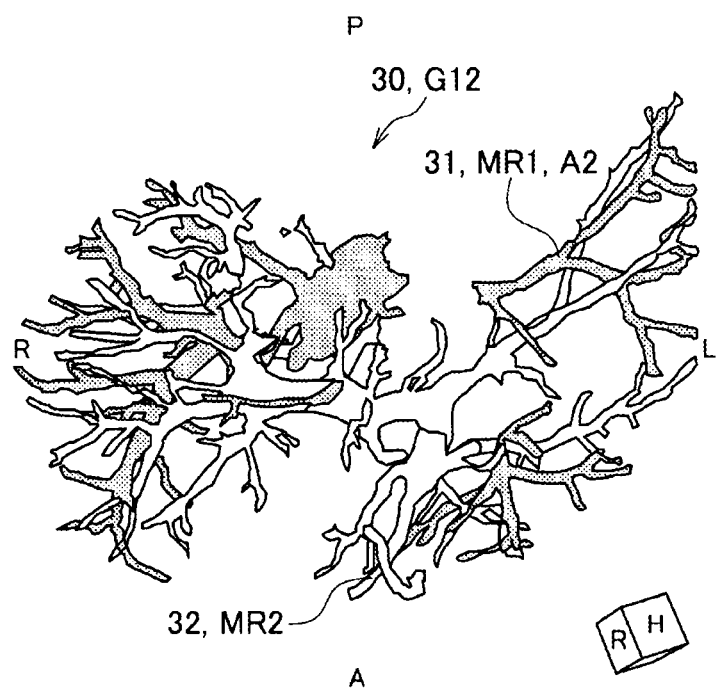
FIG. 9B is a diagram showing an example of a rendering image of a region of a liver corresponding to FIG. 9A.

FIGS. 7A, 8A, and 9A are diagrams showing an example of an MPR image of a region 30 of a liver. FIGS. 7B, 8B, and 9B are diagrams showing an example of a rendering image of the region 30 of the liver and corresponding to FIGS. 7A, 8A, and 9A.

The region 30 of the liver includes a vein 31 and a portal vein 32. A mask region MR1 obtained by extracting the vein 31 is to be subjected to a slab process. A mask region MR2 obtained by extracting the portal vein 32 is not to be subjected to a slab process.

In FIG. 7A, a slab surface is not set for the region 30 of the liver. In FIG. 8A, a slab surface SF11 is set for the region 30 of the liver. The slab surface SF11 is a surface which passes near the center of the region 30 of the liver and is parallel to a depth direction of FIG. 8A. In FIG. 9A, a slab surface SF12 is set for the region 30 of the liver. The slab surface SF12 is a surface which passes slightly above the region 30 of the liver in a cross-section shown in FIG. 9A and is parallel to a depth direction of FIG. 9A.

FIG. 7B is a diagram when the region 30 of the liver shown in FIG. 7A is seen in a view direction (from the lower side to the upper side of FIG. 7A). In FIG. 7B, the vein 31 is not subjected to a slab process, and thus the vein 31 and the portal vein 32 are mixed in an intricate state in the entire region from the front side to the rear side of FIG. 7B (in a view direction). Accordingly, a user hardly ascertains a running relationship between the vein 31 and the portal vein 32.

FIG. 8B is a diagram when the region 30 of the liver shown in FIG. 8A is seen in a view direction VD (from the lower side to the upper side of FIG. 8A). In FIG. 8B, the vein 31 is cut by the slab surface SF11, the front side of the slab surface SF11 (the side of a point of view, and the side of the root of the view direction VD) is set to be an out-of-target for rendering, and the rear side of the slab surface SF11 (a side opposite to the point of view, and the tip end side of the view direction VD) (slab region A1) is set to be a rendering target. The portal vein 32 is not cut by the slab surface SF11 and is set to be a rendering target on the front side and the rear side (a side opposite to a point of view, and the tip end side of the view direction VD) of the slab surface SF11. Accordingly, in FIG. 8B, it becomes easy to ascertain a running relationship between the vein 31 and the portal vein 32 and recognize a positional relationship therebetween.

FIG. 9B is a diagram when the region 30 of the liver shown in FIG. 9A is seen in a view direction VD (from the lower side to the upper side of FIG. 8A). In FIG. 9B, the vein 31 is cut by the slab surface SF12, and the front side of the slab surface SF12 is set to be an out-of-target for rendering and the rear side (slab region A2) of the slab surface SF12 is set to be a rendering target. The portal vein 32 is not cut by the slab surface SF12, and the front side and the rear side of the slab surface SF12 are set to be rendering targets. Accordingly, in FIG. 9B, a rendering target in the region of the vein 31 is reduced as compared with FIG. 8B, and thus it is easier to recognize a positional relationship between the vein 31 and the portal vein 32. It becomes easier to ascertain a running relationship between the vein 31 and the portal vein 32 by comparing FIGS. 7B, 8B, and 9B with each other in order. Both the mask regions MR1 and MR2 may intersect the slab surfaces SF11 and SF12.

Next, an example of rotation of a slab surface will be described.

Figure 10A:
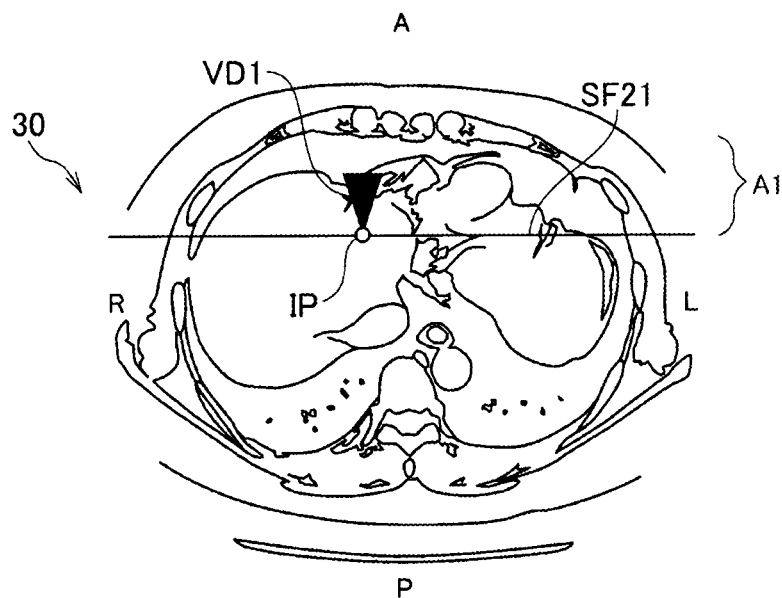
FIG. 10A is a diagram showing a first example of an MPR image of a region of a liver according to the rotation of a slab surface (no offset)
Figure 10B:
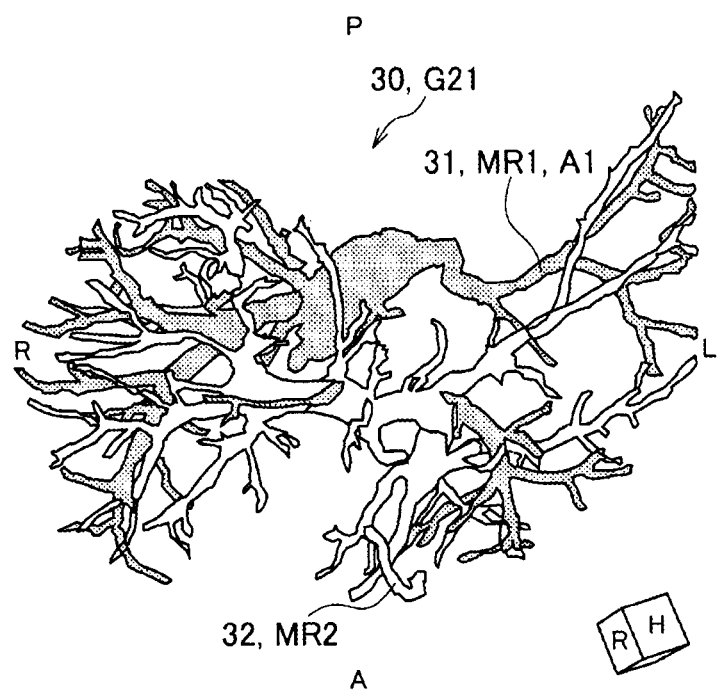
FIG. 10B is a diagram showing an example of a rendering image of a region of a liver corresponding to FIG. 10A.
Figure 11A:
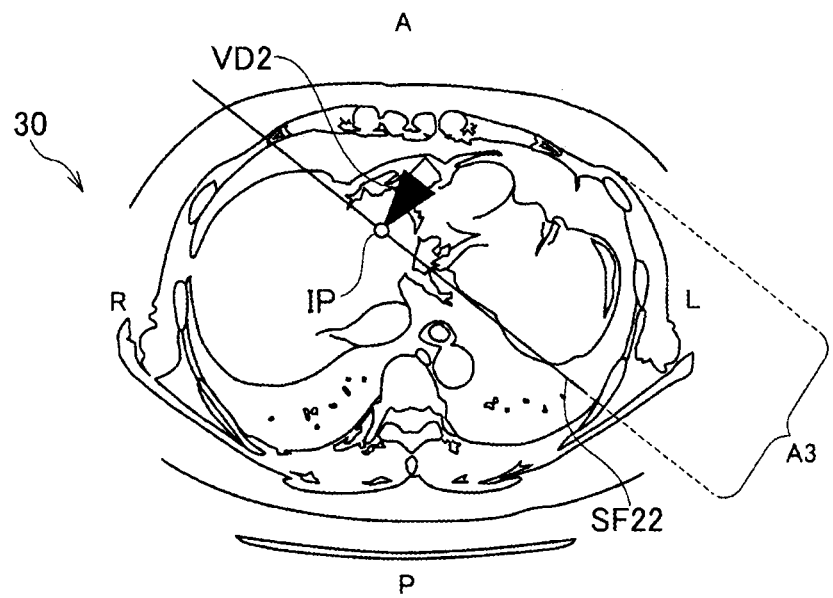
FIG. 11A is a diagram showing a second example of an MPR image of a region of a liver according to the rotation of a slab surface (no offset)
Figure 11B:
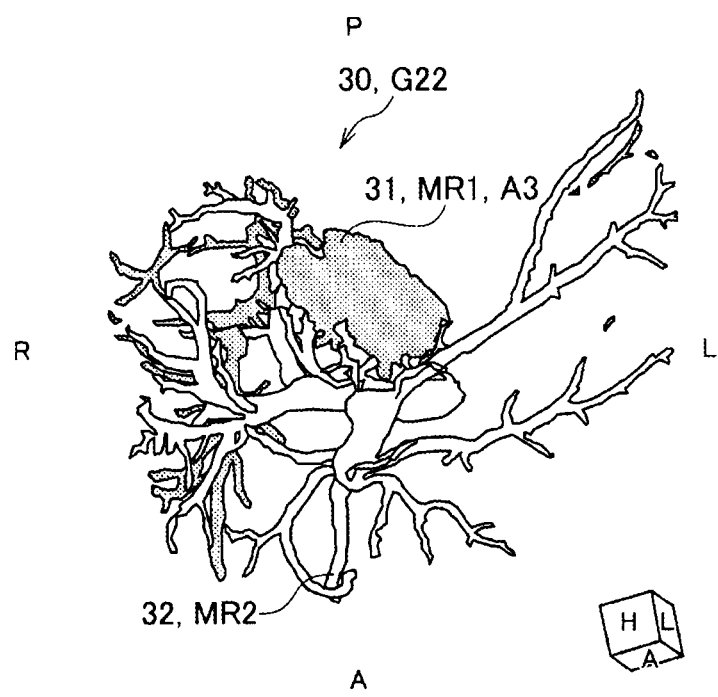
FIG. 11B is a diagram showing an example of a rendering image of a region of a liver corresponding to FIG. 11A.

FIGS. 10A and 11A are diagrams showing an example of an MPR image of the region 30 of the liver according to an example of rotation of a slab surface. FIGS. 10B and 11B are diagrams showing an example of a rendering image of the region 30 of the liver and corresponding to FIGS. 10A and 11A.

FIG. 10B is a diagram when the region 30 of the liver shown in FIG. 10A is seen in a view direction VD1 (from the upper side to the lower side of FIG. 10A). In FIG. 10B, the vein 31 is cut by a slab surface SF21, the front side of the slab surface SF21 (the side of a point of view, and the side of the root of the view direction VD1) is set to be an out-of-target for rendering, and the rear side of the slab surface SF21 (a side opposite to a point of view, and the tip end side of a view direction VD2) (slab region A1) is set to be a rendering target. The portal vein 32 is not cut by the slab surface SF21 and is set to be a rendering target on the front side and the rear side of the slab surface SF21. Accordingly, in FIG. 10B, it becomes easy to ascertain a running relationship between the vein 31 and the portal vein 32 and recognize a positional relationship therebetween.

FIG. 11B is a diagram when the region 30 of the liver shown in FIG. 9A is seen in the view direction VD2 (from the upper right side to the lower left side of FIG. 11A). In FIG. 11B, the view direction VD2 is rotated at a predetermined angle from the view direction VD1. The slab surface SF21 is also rotated about the rotation center in accordance with the rotation of the view direction. The rotation center may be a point of interest IP. In FIG. 11B, the point of interest IP is positioned on the slab surface SF. In FIG. 11B, the vein 31 is cut by a slab surface SF22 after rotation, the front side of the slab surface SF22 after rotation (the side of a point of view, and the side of the root of the view direction VD2) is set to be an out-of-target for rendering, and the rear side of the slab surface SF22 after rotation (a side opposite to the point of view, and the tip end side of the view direction VD2) (slab region A3) is set to be a rendering target. The portal vein 32 is not cut by the slab surface SF22 after rotation and is set to be a rendering target on the front side and the rear side of the slab surface SF22. Accordingly, in FIG. 11B, the same observation target as that in FIG. 10B can be confirmed from a different angle, and it becomes easy to ascertain a running relationship between the vein 31 and the portal vein 32 and recognize a positional relationship therebetween. It becomes easier to ascertain a running relationship between the vein 31 and the portal vein 32 by comparing FIGS. 10B and 11B with each other in order. Both the mask regions MR1 and MR2 may intersect the slab surfaces SF21 and SF22.

Figure 12:
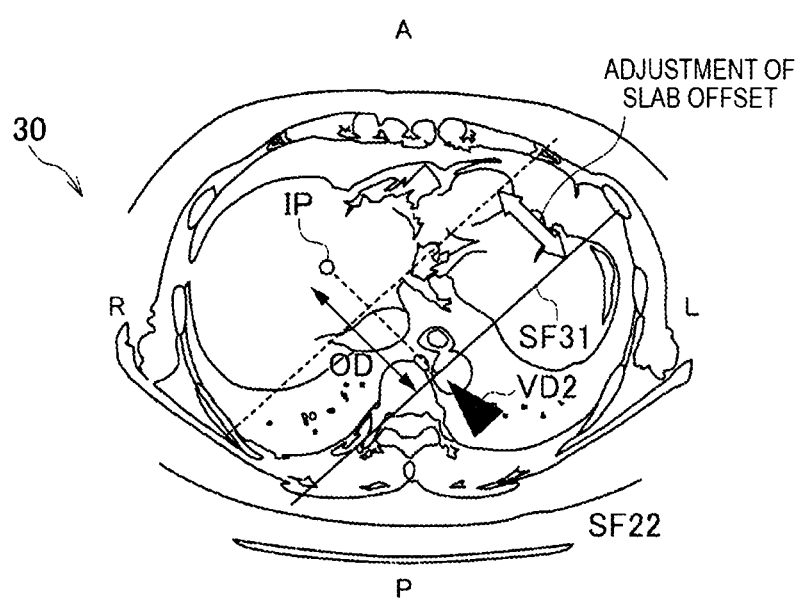
FIG. 12 is a diagram showing a third example of an MPR image of a region of a liver according to the rotation of a slab surface (offset)
Figure 13:
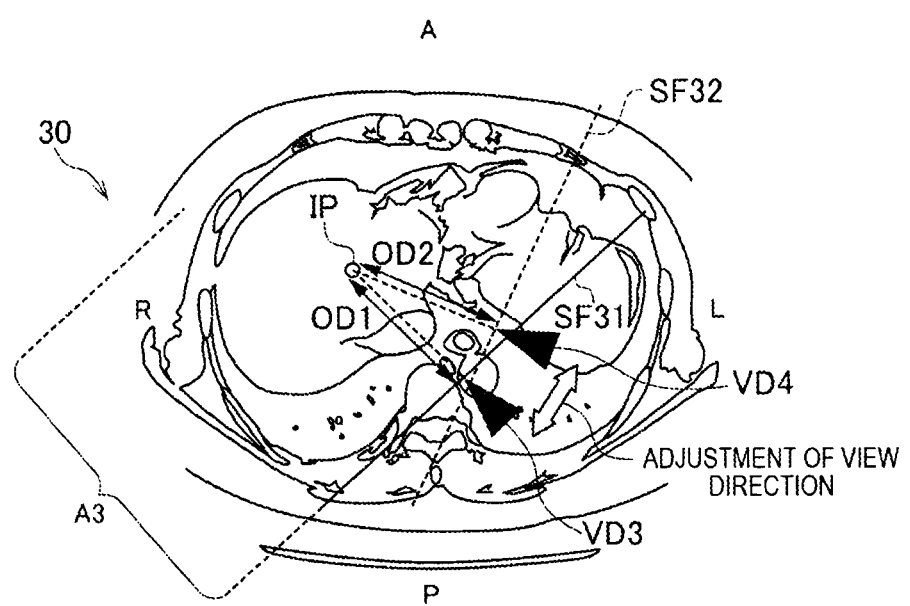
FIG. 13 is a diagram showing a fourth example of an MPR image of a region of a liver according to the rotation of a slab surface (offset)

FIGS. 12 and 13 are diagrams showing an example of an MPR image of the region 30 of the liver according to an example of rotation of a slab surface to which an offset from a rotation center is applied.

In FIGS. 12 and 13, the vein 31 is cut by a slab surface SF31, the front side of the slab surface SF31 is set to be an out-of-target for rendering, and the portal vein 32 is not cut by the slab surface SF31 and is set to be a rendering target on the front side and the rear side of the slab surface SF31. The point of interest IP and the slab surface SF31 do not correspond to each other, and the slab surface SF31 is offset from the position of the point of interest IP in a direction perpendicular to the slab surface SF31. The direction perpendicular to the slab surface SF31 is a direction parallel to a view direction VD3.

In rotation to which an offset from a rotation center is applied, the view direction VD3 and the slab surface SF31 are rotated while maintaining an offset distance OD (OD1, OD2) from the point of interest IP. In FIG. 13, when the view direction VD3 is rotated, the view direction is changed to a view direction VD4. When the slab surface SF31 is rotated in association with the rotation of the view direction VD3, the slab surface becomes a slab surface SF32. A distance between the point of interest IP and the slab surface SF31 is an offset distance OD1. A distance between the point of interest IP and the slab surface SF32 is an offset distance OD2. A region processing unit 166 may adjust the offset distance OD to any distance. The offset distance OD is secured, so that a user can observe the direction of the point of interest IP from various angles in accordance with rotation from a position where the point of interest IP is separated by the offset distance OD. Both the mask regions MR1 and MR2 may intersect the slab surfaces SF31 and SF32.

Next, a user interface for performing setting related to a slab process will be described.

Figure 14:
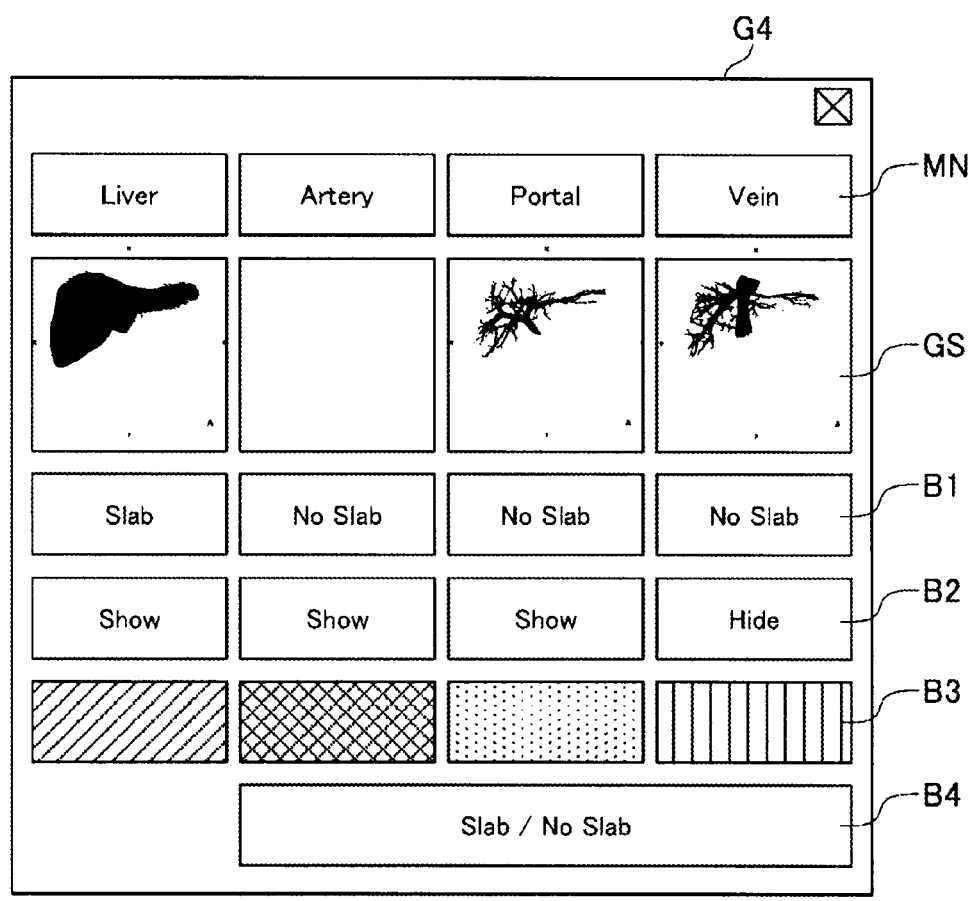
FIG. 14 is a diagram showing an example of a slab setting screen.

FIG. 14 is a diagram showing an example of a slab setting screen. The slab setting screen is a screen for performing setting related to a slab process. The setting may include individual setting for each region (each mask region) and collective setting for all regions (all mask regions).

In a slab setting screen G4, a name MN of each region (an example of identification information) in volume data, a thumbnail image GS indicating display contents for each region, and buttons B1, B2, and B3 are displayed. The button B1 is a button for setting whether or not to perform a slab process for each region (Slab/No Slab). The button B2 is a button for setting whether or not to display each region (Show/Hide). The button B3 is a button for setting a rendering color for each region. In the settings using the buttons B1 to B3, a user can arbitrarily perform selection through the UI 120. Execution or non-execution of a slab process for each region, display or non-display, and a rendering color can be set to be in a user's desired state through the setting using the buttons B1 to B3.

The button B4 is a button for collectively setting whether or not to perform a slab process on a plurality of regions (Slab/No Slab). For example, when Slab is selected, a slab process is performed in all blood vessel regions, and when No Slab is selected, a slab process is not performed in all blood vessel regions. Accordingly, it is possible to simply collectively set execution or non-execution of a slab process by using the button B4. For example, in a region of a liver, it is possible to simultaneously switch whether or not to perform a slab process on an artery, a vein, and a portal vein. For example, in a region of a liver, it is possible to simultaneously switch whether or not to perform a slab process on a left lobe and a right lobe. For example, in a region of a lung, it is possible to simultaneously switch whether or not to perform a slab process on regions of five lobes which are regions independent of each other. The button B4 may be shown to be operable on a slab setting screen different from a slab setting screen on which the button B1 is shown. It is possible to simplify an operation by causing a user to be able to operate only the button B4 without displaying the button B1 depending on an observation target.

Next, an operation example of the medical image processing apparatus will be described.

Figure 15:
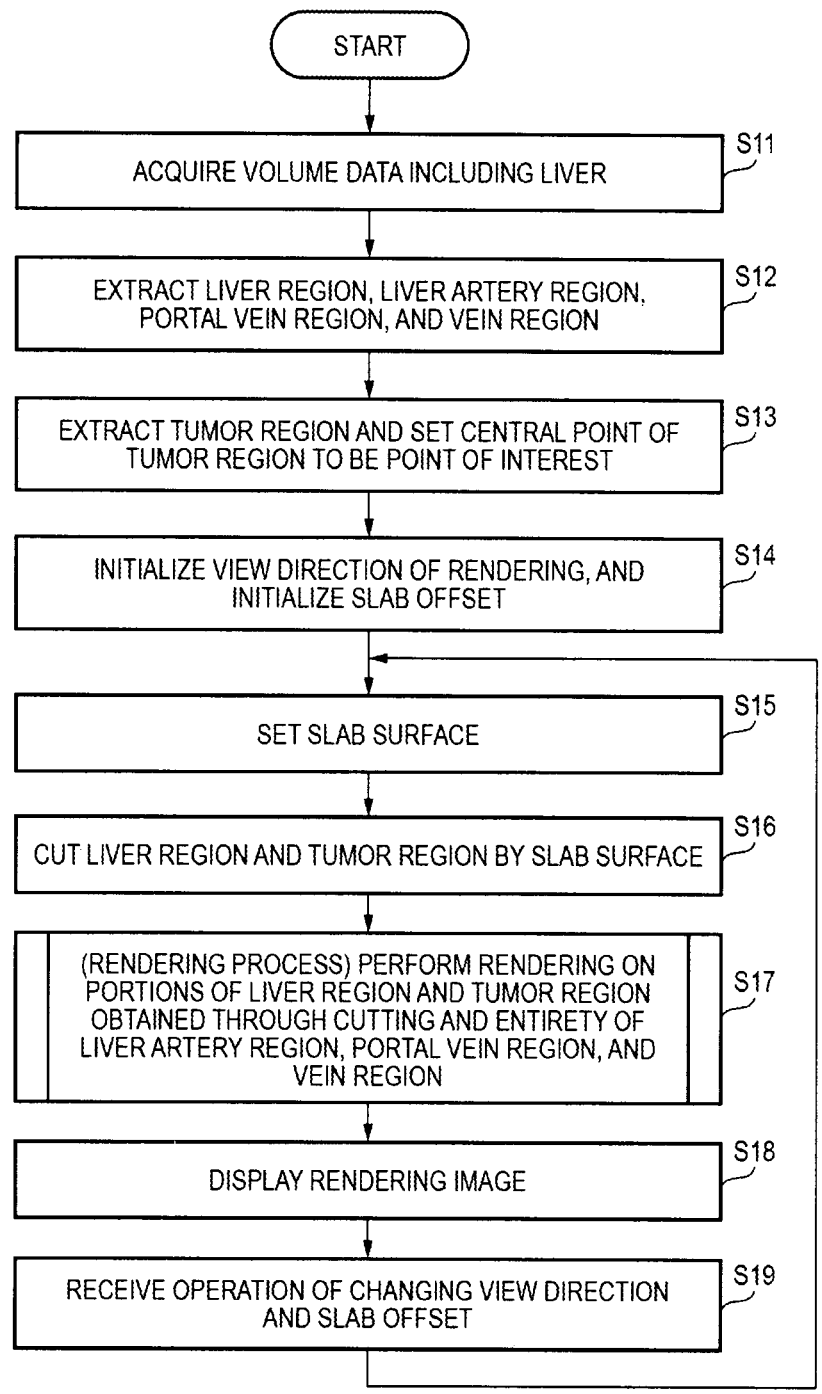
FIG. 15 is a flowchart showing an operation example of the medical image processing apparatus.

FIG. 15 is a flowchart showing an operation example of the medical image processing apparatus. In FIG. 15, for example, S11 may be performed by the port 110, S12 to S16 may be performed by the region processing unit 161 or the slab control unit 164, S17 may be performed by the image generation unit 162, and S18 may be performed by the display control unit 163.

First, volume data including a liver is acquired (S11). A liver region ML, a liver artery region MA, a portal vein region MP, and a vein region MV are extracted from the volume data (S12). A tumor region MT is extracted from the volume data, and a central point of the tumor region MT is set to be a point of interest I (S13). A view direction V of rendering is initialized to a view direction V0 (S14). A slab offset OS is initialized to a value 0 (S14). A slab surface S passing through IP+OS*V, that is, passing a position separated from the point of interest I in the view direction V by a distance corresponding to the slab offset OS and having the view direction V as a normal line is set (S15). The slab offset OS corresponds to an offset distance OD.

Here, it is assumed that the liver region ML and the tumor region MT are mask regions in which a slab process is to be performed, and the liver artery region MA, the portal vein region MP, and the vein region MV are mask regions in which a slab process is not to be performed. Accordingly, a slab process is performed on the liver region ML and the tumor region MT. In this case, the liver region ML and the tumor region MT are cut by a slab surface S (S16). A rendering process is performed on the basis of a rendering target obtained through a slab process and a rendering target obtained without performing a slab process. In the rendering process, rendering is performed on portions of the liver region ML and the tumor region MT as rendering targets obtained through cutting and the entirety of the liver artery region MA, the portal vein region MP, and the vein region MV (S17). A rendering image obtained through the rendering process is displayed (S18).

The UI 120 receives an operation of changing the view direction V and the slab offset OS (S19). The region processing unit 161 or the slab control unit 164 changes the view direction V and the value of the slab offset OS in accordance with a changing operation. The operation proceeds to S15.

Figure 16:
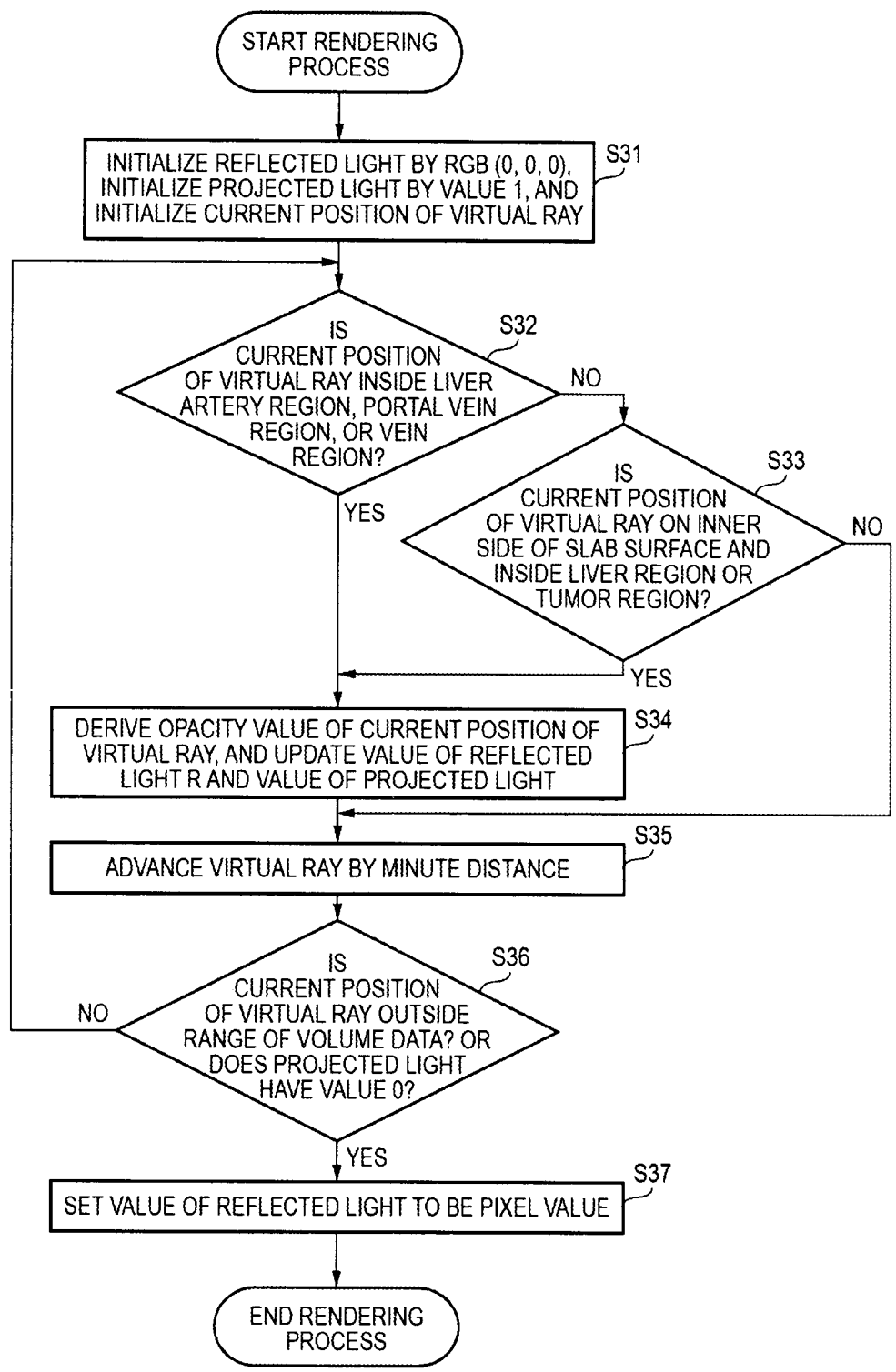
FIG. 16 is a flowchart showing a detailed example of a rendering process.

FIG. 16 is a flowchart showing an example of details of a rendering process. The rendering process may be mainly performed by the image generation unit 162. Here, it is assumed that the front side of a slab surface S is set to be an out-of-target for rendering in a mask region in which a slab process is performed, and the rear side of the slab surface S is set to be a rendering target.

First, parameters are initialized (S31). For example, reflected light R is initialized by RGB (0, 0, 0), projected light W is initialized by a value 1, and a current position X of a virtual ray is initialized by X0. It is determined whether or not the current position X is inside the liver artery region MA, the portal vein region MP, or the vein region MV (S32). In a case where the current position X is not inside the liver artery region MA, the portal vein region MP, or the vein region MV, it is determined whether or not the current position X is on the rear side of the slab surface S (a side opposite to a point of view, and the tip end side of a view direction) and the current position X is inside the liver region ML or the tumor region MT (S33).

In a case where the current position X is inside the liver artery region MA, the portal vein region MP, or the vein region MV in S32 (Yes in S32) or in a case where the current position X is on the rear side of the slab surface S and inside the liver region ML or the tumor region MT in S33 (Yes in S33), an opacity value of the current position X of a virtual ray is derived, and the value of the reflected light R and the value of the projected light W are updated (S34). In this case, the image generation unit 162 acquires a voxel value and an opacity value at the current position X with reference to a look up table (LUT) stored in the memory 150. Information of an opacity value for each voxel may be stored in the LUT. For example, the reflected light R may be obtained by adding a value based on an opacity value. The projected light W may be obtained by subtracting a value based on an opacity value.

After S34 or in S33, in a case where the current position X is on the front side of the slab surface S or the current position X is not inside the liver region ML and the tumor region MT (No in S33), a virtual ray is advanced by a minute distance in the view direction V (S35). That is, a relationship of X←X+ΔV is set.

It is determined whether or not the current position X is outside the range of volume data or whether or not the projected light W has a value 0 (S36). In a case where the current position X is outside the range of volume data or the projected light W has a value 0 (Yes in S36), the value of reflected light R is set to be a pixel value in a pixel corresponding to the virtual ray in the rendering image (S37). On the other hand, in a case where the current position X is inside the range of volume data or the projected light W does not have a value 0 (No in S36), the operation proceeds to S32. The processes of S31 to S37 are performed by moving the position of the virtual ray in the volume data in parallel in a direction perpendicular to the virtual ray to calculate pixel values of the respective pixels in the rendering image, determine pixel values of the respective pixels, and generate a rendering image.

In this manner, the medical image processing apparatus 100 can perform visualization by applying a slab process to at least one mask region and without applying a slab process to at least one mask region including, for example, tubular tissues at the time of simultaneously visualizing a plurality of mask regions. For example, a user can easily ascertain a relationship between tissues in the vicinity of a disease portion included in a mask region subjected to a slab process and the running of blood vessels included in a mask region not subjected to a slab process.

The medical image processing apparatus 100 can provide a convenient UI at the time of observing a resection target such as a tumor. For example, a slab display is performed on an internal organ to set an unnecessary portion to be an out-of-target for rendering, and blood vessels and the like are not subjected to slab display to be capable of being displayed as rendering targets at all times. A portion which is included in a mask region of a disease portion is entirely displayed at all times, and a slab may be applied to a portion which is not included in a mask region of a disease portion to set an unnecessary portion to be an out-of-target for display. A slab may be applied to an internal organ existing in a disease portion to set an unnecessary portion to be an out-of-target for display, and a slab may not be applied to blood vessels in an internal organ to display the entirety of the blood vessels.

Although various embodiments have been described in detail with reference to the accompanying drawings, it is needless to say that the disclosure is not limited thereto. It would be apparent for those skilled in the technical field to which the invention belongs that various modified examples or corrected examples are conceivable within the scope of the technical idea recited in the claims, and it would be understood that these fall within the technical scope of the disclosure.

Figure 17:
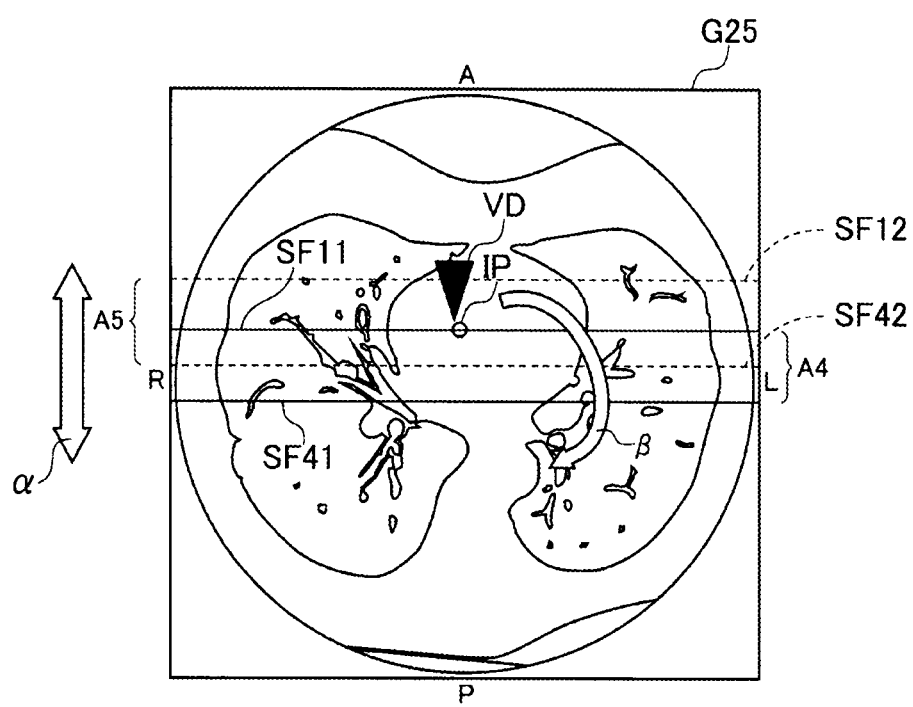
FIG. 17 is a diagram showing an example of a slab region having two slab surfaces.

For example, a slab process performed using one slab surface has been mainly exemplified, but a slab region may be generated by performing a slab process using two slab surfaces. FIG. 17 is a diagram showing an example of a slab region using two slab surfaces. The slab control unit 164 may set two slab surfaces SF11 and SF41, may set each voxel of a region (slab region A4) interposed between the two slab surfaces SF11 and SF41 to be a rendering target, and may set each voxel outside the region interposed between the two slab surfaces SF11 and SF41 to be an out-of-target for rendering. In FIG. 17, the slab surfaces SF11 and SF41 can be moved in the direction of an arrow a, and the slab surfaces SF11 and SF41 can be rotated around the point of interest IP in the direction of an arrow 13 or in a direction opposite thereto. A slab thickness which is a length between the slab surfaces SF11 and SF41 can be arbitrarily adjusted through the UI 120.

The slab control unit 164 may receive a moving operation through, for example, the UI 120 to move the slab surfaces SF11 and SF41 in the direction of the arrow a (here, upward) and set the slab surfaces SF12 and SF42. The slab surface SF11 is moved in parallel to become the slab surface SF12, and the slab surface SF41 is moved in parallel to become the slab surface SF42. A region interposed between the slab surfaces SF12 and SF42 is a slab region A5. The slab surface SF42 intersects at least the mask region MR1 (for example, one internal organ out of internal organs separating into right and left parts in FIG. 17). Since the widths of the slab regions A2 and A5 before and after movement do not change, a distance between the slab surface SF11 and the slab surface SF41 and a distance between the slab surface SF12 and the slab surface SF42 are the same.

For example, a rendering image may be displayed according to, for example, a parallel projection method or a perspective projection method. The rendering image may be a volume-rendered image or a surface-rendered image. The rendering image may be a rendering image which is generated by switching between volume rendering and surface rendering for each region.

A slab process may be implemented by a masking process. Even when a masking process is performed instead of a slab process, a user can simply perform an operation using the slab setting screen (slab setting UI) shown in FIG. 14. In this case, the region processing unit 161 may calculate AND (AND operation) of a masking process for visualizing a region (mask region) of which the contour has any shape and a masking process for visualizing a region (slab region) of which the contour is formed by a plane, and the image generation unit 162 may perform rendering. Thereby, a slab region in a mask region can be drawn. Even when a masking process is performed instead of a slab process, a UI for operating a slab surface through the UI 120 is provided.

For example, the UI for operating a slab surface through the UI 120 is considered as follows. A cross-section image in which the position of a slab surface is visualized may be set to be a UI for operating a slab surface. The movement of a slab surface in a depth direction, the rotation of a slab surface, and an operation for an offset distance from a point of interest may be performed through a mouse wheel, a scroll bar, and a dragging operation of a slab surface in a cross-section image by using the mouse wheel, the scroll bar, and the cross-section image as UIs for operating a slab surface. A slab surface may be rotated in association with the rotation of a rendering image by using a UI for rotating a rendering image as a UI for operating a slab surface. A UI for operating a slab surface may be displayed on the display 130 as a UI object so that a slab surface is rotated through the UI object. A point of interest may be set through point designation in a rendering image and a cross-section image by using the rendering image and the cross-section image as UIs for operating a slab surface, or a slab surface may be moved in association with the movement of a point of interest.

Each region may be visualized by a mask (mask region) or may be visualized by a set of surfaces. In this case, a surface may be created from a region visualized by a mask by a Marching Cube method. A plurality of points of interest or portions of interest may exist, and the region processing unit 161 may set one point of interest or one portion of interest among the plurality of points of interest or portions of interest. In this case, the region processing unit 161 may switch between a point of interest and a portion of interest through the UI 120.

The medical image processing apparatus 100 may include at least the processor 140 and the memory 150. The port 110, the UI 120, and the display 130 may be externally attached to the medical image processing apparatus 100.

It is illustrated that volume data as a captured CT image is transmitted to the medical image processing apparatus 100 from the CT scanner 200. Alternatively, volume data may be transmitted to a server on a network (for example, an image data server (PACS) (not shown)) or the like and stored so that the volume data is temporarily accumulated. In this case, the port 110 of the medical image processing apparatus 100 may acquire volume data from a server or the like through a wired line or a wireless line when necessary or may acquire volume data through any storage medium (not shown).

It is illustrated that volume data as a captured CT image is transmitted to the medical image processing apparatus 100 through the port 110 from the CT scanner 200. This also includes a case where the CT scanner 200 and the medical image processing apparatus 100 are substantially integrated as one product. A case where the medical image processing apparatus 100 is treated as a console of the CT scanner 200 is also included.

It is illustrated that volume data including information regarding the inside of a subject is generated by capturing an image by the CT scanner 200, but volume data may be generated by capturing an image by other apparatuses. The other apparatuses include a magnetic resonance imaging (MM) apparatus, a positron emission tomography (PET) apparatus, an angiographic apparatus, or other modality apparatuses. The PET apparatus may be used in combination with other modality apparatuses.

The disclosure can be visualized as a medical image processing method in which operations in the medical image processing apparatus 100 are specified. The disclosure can be visualized as a program causing a computer to execute steps of the medical image processing method.

(Outline of the Above-Described Embodiment)

An aspect of the above-described embodiment is a medical image processing apparatus 100 that visualizes tissues and may include an acquisition unit (for example, the port 110), a processing unit 160, an operation unit (for example, the UI 120), and a display unit (for example, the display 130). The acquisition unit may have a function of acquiring volume data including tissues. The processing unit 160 may have a function of setting a mask region MR1 (an example of a first mask region) and a mask region MR2 (an example of a second mask region) which include a voxel to be rendered among a plurality of voxels included in the volume data. The processing unit 160 may have a function of setting a slab surface SF11 (an example of a first plane) which intersects both the mask region MR1 and the mask region MR2. The processing unit 160 may have a function of displaying a rendering image G11 (an example of a first image) in which a slab region A1 (an example of a first region) which is formed by cutting the mask region MR1 by the slab surface SF11 and the mask region MR2 are rendered through the display unit. The processing unit 160 may receive a first operation for setting a slab surface SF12 (an example of a second plane) which is parallel to the slab surface SF11 and intersects both the mask region MR1 and the mask region MR2 through the operation unit. The processing unit 160 may have a function of displaying a rendering image G12 (an example of a second rendering image) in which a slab region A2 formed by cutting the mask region MR1 by the slab surface SF12 (an example of a second region) and the mask region MR2 are rendered.

Thereby, the medical image processing apparatus 100 can exclude a portion of at least one of a plurality of tissues from the display target and can easily ascertain a positional relationship between tissues in a mutually intricate state. For example, it is possible to easily ascertain a relationship between tissues in the vicinity of a disease portion and the running of blood vessels. For example, it is possible to easily ascertain a relationship between an internal organ and the running of blood vessels related to the internal organ. For example, it is possible to easily ascertain a running relationship between a plurality of blood vessels. For example, it is possible to easily ascertain a relationship between tissues in the vicinity of a disease portion, the running of a bronchus, and the running of blood vessels.

The processing unit 160 may have a function of setting a slab surface SF41 (an example of a third plane) which is parallel to the slab surface SF11 and intersects at least the mask region MR1. The slab region A4 (an example of a first region) may be a region interposed between the slab surface SF11 and the slab surface SF41. The processing unit 160 may set a slab surface SF42 (an example of a fourth surface) which is parallel to the slab surface SF12 and intersects at least the mask region MR1. A distance between the slab surface SF11 and the slab surface SF41 and a distance between the slab surface SF12 and the slab surface SF42 may be the same. The slab region A2 may be the slab region A5 interposed between the slab surface SF12 and the slab surface SF41.

Thereby, the medical image processing apparatus 100 can set a portion including unnecessary information in the slab region A1 to be in a non-display state. Thus, a user can obtain minimum information on the slab region A1 and can more easily recognize a relationship with other mask regions.

The processing unit 160 may set a point of interest IP. A second operation for rotating slab surfaces SF21 and SF31 may be received through an operation unit. The processing unit 160 may acquire slab surfaces SF22 and SF32 (examples of a fifth plane) which are planes obtained by rotating the surfaces SF21 and SF31 (examples of a first plane) around the point of interest IP on the basis of the second operation and intersect both the mask region MR1 and the mask region MR2. The processing unit 160 may display a rendering image G22 (an example of a third image) in which the slab region A3 (an example of a third region) formed by cutting the mask region MR1 by the slab surfaces SF22 and SF32 and the mask region MR2 are rendered through the display unit. An offset distance OD1 (an example of a first distance) which is a distance between the slab surfaces SF21 and SF31 and the point of interest IP and an offset distance OD2 (an example of a second distance) which is a distance between the slab surfaces SF22 and SF32 and the point of interest IP may be the same. The offset distances OD1 and OD2 may be equal to or greater than a value 0.

The second operation may also function as an operation of rotating view directions VD1 and VD2 of rendering. The processing unit 160 may rotate the view directions VD1 and VD2 around a point of interest in accordance with an angle operated in the second operation to display a image G22 in which the slab region A3 formed by cutting the mask region MR1 by the slab surfaces SF22 and SF32 and the mask region MR2 are rendered on the display unit.

Thereby, the medical image processing apparatus 100 can operate and rotate a slab surface with a point of interest IP as a reference. A slab surface SF can be rotated while maintaining a distance between the point of interest IP and the slab surface SF. Thus, for example, in a case where an offset distance is 0, a user can confirm the state of the vicinity of the point of interest IP with the point of interest IP as a point of view. In a case where an offset distance is greater than 0, the user can confirm the direction of the point of interest IP from the vicinity of the point of interest IP.

The operation unit may include a button B1 (an example of a first user interface) for individually setting whether or not at least one mask region has been cut.

The operation unit may include a button B4 (for example, second user interface) for simultaneously setting whether or not a plurality of mask regions have been cut.

Thereby, the medical image processing apparatus 100 can individually set whether or not the drawing of each mask region is limited to be performed within the range of a slab. It is possible to collectively set whether or not the drawing of each mask region is limited to be performed within the range of a slab. In this case, it is possible to reduce a time required for setting and simplify an operation.

Another aspect of the above-described embodiment is a medical image processing method of visualizing tissues, and the medical image processing method may be a medical image processing method including a step of acquiring volume data including tissues, a step of setting a first mask region and a second mask region which include a voxel to be rendered among a plurality of voxels included in the volume data, a step of setting a first plane which intersects both the first mask region and the second mask region, a step of displaying a first image in which a first region formed by cutting the first mask region by the first plane and the second mask region are rendered through a display unit, a step of receiving a first operation for setting a second plane which is parallel to the first plane and intersects both the first mask region and the second mask region through an operation unit, and a step of displaying a second image in which a second region formed by cutting the first mask region by the second plane and the second mask region are rendered through the display unit.

Still another aspect of the present embodiment may be a system including: a display unit; and circuitry configured to: acquire volume data including the tissues from a CT (Computed Tomography) scanner; and set a first mask region and a second mask region which include a voxel to be rendered among a plurality of voxels included in the volume data; set a first plane which intersects both the first mask region and the second mask region; display through the display unit a first image in which a first region formed by cutting the first mask region by the first plane and the second mask region are rendered; receive through an operation unit a first operation for setting a second plane which is parallel to the first plane and intersects both the first mask region and the second mask region; and display a second image in which a second region formed by cutting the first mask region by the second plane and the second mask region are rendered.

The disclosure is useful for a medical image processing apparatus, a medical image processing method, a medical image processing program, and the like which are capable of improving the visibility of a tissue to be observed.

What is claimed is:

1. A medical image processing apparatus configured to visualize tissues, the medical image processing apparatus comprising:
a display unit; and
circuitry configured to:
acquire volume data including the tissues; and
set a first mask region and a second mask region which include a voxel to be rendered and displayed on the display unit among a plurality of voxels included in the volume data;
set a first cutting plane which intersects both the first mask region and the second mask region;
display through the display unit a first image in which a first region formed by cutting the first mask region by the first cutting plane and the second mask region are rendered;
receive through an operation unit a first operation for adjusting the first cutting plane as a second cutting plane which is parallel to the first cutting plane and intersects both the first mask region and the second mask region; and
display through the display unit a second image in which a second region formed by cutting the first mask region by the second cutting plane and the second mask region are rendered,
wherein the first mask region and the second mask region have different shapes.

2. The medical image processing apparatus according to claim 1, wherein
the circuitry is configured to set a third cutting plane which is parallel to the first cutting plane and intersects at least the first mask region,
the first region is a region between the first cutting plane and the third cutting plane,
the circuitry is configured to adjust the third cutting plane as a fourth cutting plane which is parallel to the second cutting plane and intersects at least the first mask region,
a distance between the first cutting plane and the third cutting plane and a distance between the second cutting plane and the fourth cutting plane are the same, and
the second region is a region between the second cutting plane and the fourth cutting plane.

3. The medical image processing apparatus according to claim 1, wherein the circuitry is configured to:
set a point of interest;
receive a second operation for rotating the first cutting plane through the operation unit;
adjusting the first cutting plane as a fifth cutting plane by rotating the first cutting plane around the point of interest based on the second operation and intersects both the first mask region and the second mask region; and
display a third image in which a third region formed by cutting the first mask region by the fifth cutting plane and the second mask region are rendered on the display unit, and
a first distance between the first cutting plane and the point of interest and a second distance between the fifth cutting plane and the point of interest are the same.

4. The medical image processing apparatus according to claim 3, wherein
the second operation also functions as an operation of rotating a view direction of rendering, and
the circuitry is configured to rotate the view direction around the point of interest in accordance with an angle operated in the second operation to display the third image in which the third region formed by cutting the first mask region by the fifth cutting plane and the second mask region are rendered on the display unit.

5. The medical image processing apparatus according to claim 1, wherein the second mask region is a region of a tubular tissue.

6. The medical image processing apparatus according to claim 1, wherein the operation unit includes a first user interface for setting whether or not at least one mask region has been cut, while the second mask region is kept shown on the display unit.

7. The medical image processing apparatus according to claim 1, wherein the operation unit includes a second user interface for setting whether or not a plurality of mask regions have been simultaneously cut, while the second mask region is kept shown on the display unit.

8. A medical image processing method of visualizing tissues, the medical image processing method comprising:

acquiring volume data including tissues;

setting a first mask region and a second mask region which include a voxel to be rendered and displayed on a display unit among a plurality of voxels included in the volume data;

setting a first cutting plane which intersects both the first mask region and the second mask region;

displaying through the display unit a first image in which a first region formed by cutting the first mask region by the first cutting plane and the second mask region are rendered;

receiving through an operation unit a first operation for adjusting the first cutting plane as a second cutting plane which is parallel to the first cutting plane and intersects both the first mask region and the second mask region; and displaying through the display unit a second image in which a second region formed by cutting the first mask region by the second cutting plane and the second mask region are rendered, wherein the first mask region and the second mask region have different shapes.

9. A system configured to visualize tissues, the system comprising:

a display unit; and circuitry configured to:

acquire volume data including the tissues from a CT (Computed Tomography) scanner; and set a first mask region and a second mask region which include a voxel to be rendered and displayed on the display unit among a plurality of voxels included in the volume data;

set a first cutting plane which intersects both the first mask region and the second mask region;

display through the display unit a first image in which a first region formed by cutting the first mask region by the first cutting plane and the second mask region are rendered;

receive through an operation unit a first operation for adjusting the first cutting plane as a second cutting plane which is parallel to the first cutting plane and intersects both the first mask region and the second mask region; and display a second image in which a second region formed by cutting the first mask region by the second cutting plane and the second mask region are rendered, wherein the first mask region and the second mask region have different shapes.

\* \* \* \* \*

UNITED STATES PATENT AND TRADEMARK OFFICE
CERTIFICATE OF CORRECTION

| | | |
|---|---|---|
| PATENT NO. | : 11,379,976 B2 | Page 1 of 1 |
| APPLICATION NO. | : 16/839399 | |
| DATED | : July 5, 2022 | |
| INVENTOR(S) | : Shusuke Chino et al. | |

It is certified that error appears in the above-identified patent and that said Letters Patent is hereby corrected as shown below:

In the Specification

Column 13, Line 53, "an arrow 13 or in" should read -- an arrow β or in --

Column 15, Line 17, "(MM) apparatus, a position" should read -- (MRI) apparatus, a position --

Signed and Sealed this
Twenty-fourth Day of October, 2023

Katherine Kelly Vidal
*Director of the United States Patent and Trademark Office*